US008895597B2

(12) United States Patent
Recinos et al.

(10) Patent No.: US 8,895,597 B2
(45) Date of Patent: Nov. 25, 2014

(54) COMBINATION OF LOCAL TEMOZOLOMIDE WITH LOCAL BCNU

(76) Inventors: Violette Renard Recinos, Highland Heights, OH (US); Betty Tyler, Catonsville, MD (US); Sarah Brem Sunshine, Pikesville, MD (US); Henry Brem, Owings Mills, MD (US)

( * ) Notice: Subject to any disclaimer, the term of this patent is extended or adjusted under 35 U.S.C. 154(b) by 108 days.

(21) Appl. No.: 13/163,223

(22) Filed: Jun. 17, 2011

(65) Prior Publication Data

US 2011/0313010 A1    Dec. 22, 2011

Related U.S. Application Data

(60) Provisional application No. 61/355,828, filed on Jun. 17, 2010.

(51) Int. Cl.
*A61K 31/415* (2006.01)
*A61K 31/175* (2006.01)
*A61K 31/4188* (2006.01)

(52) U.S. Cl.
CPC ........... *A61K 31/175* (2013.01); *A61K 31/4188* (2013.01)
USPC .......................................... 514/393; 514/589

(58) Field of Classification Search
CPC .. C07D 209/08; C07D 209/12; C07D 209/14; C07D 209/16; C07D 401/12
USPC ................................. 514/393, 589
See application file for complete search history.

(56) References Cited

U.S. PATENT DOCUMENTS

| | | | |
|---|---|---|---|
| 4,861,627 A | 8/1989 | Mathiowitz | |
| 5,019,400 A | 5/1991 | Gombotz | |
| 5,271,961 A | 12/1993 | Mathiowitz | |
| 6,262,034 B1 | 7/2001 | Mathiowitz | |
| 6,491,666 B1 | 12/2002 | Santini, Jr. | |
| 6,527,762 B1 | 3/2003 | Santini, Jr. | |
| 6,976,982 B2 | 12/2005 | Santini, Jr. | |
| 7,175,909 B2 | 2/2007 | Hu | |
| 7,175,912 B2 | 2/2007 | Cui | |
| 7,226,442 B2 | 6/2007 | Sheppard, Jr. | |
| 7,604,628 B2 | 10/2009 | Santini, Jr. | |
| 2005/0271745 A1 | 12/2005 | Gruettner | |

FOREIGN PATENT DOCUMENTS

| CN | 1615855 | * | 5/2005 |
|---|---|---|---|
| WO | 9321906 | | 11/1993 |

OTHER PUBLICATIONS

Scott (thesis Jun. 16, 2010).Scott (thesis Jun. 16, 2010) (parts 1-3).*
Gururangan et al. (Neuro-Oncology 3, 246-250, 2001).*
National Institute for Clinical Excellence (Dec. 2004).*
Public Summary Document Nov. 2005.*
Prados (Semin Oncology 4(13); 24, 2001) Abstract Only.*
Barrie et al. (Annals of Oncology 16: 1177-1184, 2005).*
Prados et. al. (Neuro-Oncology p. 33-37, 2004).*
Kim et al (Journal of Controlled Release 123 (2007) 172-178).*
McGrit et al (J Neurosurg 110:583-588 (2009).*
Brem et al. (Cancer chemotherapy and Pharmacology, (2007) 60(5) 643-650).*
Gururangan et. al. (Neuro-Oncology 3, 246-250, 2001).*
Attenello, et al., "Use of Gliadel (BCNU) wafer in the surgical treatment of malignant glioma: a 10-year institutional experience", Ann Surg Oncol., 15:2887-93 (2008).
Beck, et al., "A new long-acting injectable microcapsule system for the administration of progesterone", Fertil. Steril., 31:545 (1979).
Benita, et al., "Characterization of drug-loaded poly(d,l-lactide) microspheres", J. Pharm. Sci., 73:1721 (1984).
Brem, et al., "Local delivery of temozolomide by biodegradable polymers is superior to oral administration in a rodent glioma model",Cancer Chemother. Pharmacol., 60(5):643-650 (2007).
Brem, et al., "Placebo-controlled trial of safety and efficacy of intraoperative controlled delivery by biodegradable polymers of chemotherapy for recurrent gliomas. The Polymer-brain Tumor Treatment Group", Lancet, 345:1008-1012 (1995).
Brem, et al. "The safety of interstitial chemotherapy with BCNU-loaded polymer followed by radiation therapy in the treatment of newly diagnosed malignant gliomas: phase I trial", J Neurooncol.. 26:111-123 (1995).
Brock, et al., "Phase I trial of temozolomide using an extended continuous oral schedule", Cancer Res, 58:4363-4348 (1998).
Castro, et al., "Current and future strategies for the treatment of malignant brain tumors", Pharmacal. Ther., 98(1):71-108 (2003).
Chang, et al., "Patterns of Care for Adults With Newly Diagnosed Malignant Glioma", JAMA, 293(20):557-564 (2005).
Gerber, et al., The impact of thrombocytopenia from temozolomide and radiation in newly diagnosed adults with high-grade gliomas Neuro Oncol, 9:47-52 (2007).
Grossman, et al., "The intracerebral distribution of BCNU delivered by surgically implanted biodegradable polymers", J. Neurosurg. 76(4):640-647 (1992).
Gururangan, et al., "Phase I study of Gliadel wafers plus temozolomide in adults with recurrent supratentorial high-grade gliomas", Neuro Oncol, 3:246-250 (2001).
Hammond, et al., "A randomized phase I and pharmacological trial of sequences of 1,3-bis(2-chloroethyl)-1-nitrosourea and temozolomide in patients with advanced solid neoplasms", Clin Cancer Res 10:1645-1656 (2004).
Kim, et al., "Resorbable polymer microchips releasing BCNU inhibit tumor growth in the rat 9L flank model", J Control Release. ,123(2):172-8 (2007).
La Rocca, et al., "A phase 2 study of multi-modal therapy with surgery, carmustine (BCNU) wafer, radiation therapy (RT), and temozolomide (TMZ) in patients (pts) with newly diagnosed supratentorial malignant glioma (MG)", Presented at the 8th Congress of the European Association of Neurooncology, Barcellona, Spain, Sep. 12-14, 2008.

(Continued)

*Primary Examiner* — Shirley V Gembeh

(74) *Attorney, Agent, or Firm* — Pabst Patent Group LLP

(57) ABSTRACT

The additive effect of combined intracranial carmustine ("BCNU") with intracranial temozolomide ("TMZ"), and particularly in combination with radiation ("XRT"), in the treatment of two rat intracranial glioma models, the 9L gliosarcoma and the F98 glioma, demonstrates that local delivery of both drugs, especially in combination with radiation, is far more effective than delivery of either drug alone or one systemically and one locally, either with or without radiation. The triple therapy showed a significant improvement in survival when compared to controls (p=0.0004), local BCNU (p=0.0043), oral TMZ (p=0.0026), local TMZ (p=0.0105), and the combinations of either BCNU and XRT (p=0.0378) or oral TMZ and local BCNU (p=0.0154).

8 Claims, 5 Drawing Sheets

(56) References Cited

OTHER PUBLICATIONS

Lee et al., "Inactivation of O6-alkylguanine-DNA alkyltransferase in human peripheral blood mononuclear cells by temozolomide", Br. J. Cancer 69:452-456 (1994).

Mathiowitz, et al., "Morphology of polyanhydride microsphere delivery systems", J. Scanning Microscopy, 4:329 (1990).

Mathiowitz, et al., "Novel microcapsules for delivery Systems", Reactive Polymers, 6:275-283(1987).

McGirt, et al., "Gliadel (BCNU) wafer plus concomitant temozolomide therapy after primary resection of glioblastoma multiforme" J Neurosurg, 110(3):583-588 (2009).

Menei, et al., "Biodegradable carmustine-impregnated wafers (Gliadel®): the French experience". Presented at the 8th Congress of the European Association of Neurooncology, Barcellona, Spain, Sep. 12-14, 2008.

Pan, et al. "A retrospective study of the safety of BCNU wafers with concurrent temozolomide and radiotherapy and adjuvant temozolomide for newly diagnosed glioblastoma patients", J Neurooncol 88:353-357 (2008).

Parney, et al., "Current chemotherapy for glioblastoma" Cancer J, 9:149-156 (2003),.

Plowman, et al., "Preclinical antitumor activity of temozolomide in mice: efficacy against human brain tumor xenografts and synergism with 1,3-bis(2-chloroethyl)-1-nitrosourea", Cancer Res, 54:3793-99 (1994).

Rautio, et al, "Drug delivery systems for brain tumor therapy", Curr Pharm Des, 10:1341-1353 (2004).

Raza, et al., "Local delivery of antineoplastic agents by controlled-release polymers for the treatment of malignant brain tumours", Expert Opin. Biol. Ther., 5(4):477-494 (2005).

Recinos, at al., "Combination of intracranial temozolomide with intracranial carmustine improves survival when compared with either treatment alone in a rodent glioma model", Neurosurgery, 66:530-37 (2010).

Rostomily, et al., "Radical surgery in the management of low-grade and high-grade gliomas", Baillieres Clin Neurol, 5:345-369 (1996).

Soffietti, et al., "New chemotherapy options for the treatment of malignant gliomas", Anticancer Drugs, 18:621-632 (2007).

Stupp, et al., "Promising survival for patients with newly diagnosed glioblastoma multiforme treated with concomitant radiation plus temozolomide followed by adjuvant temozolomide", J Clin Oncol, 20:1375-1382 (2002).

Stupp, et al, "Radiotherapy plus concomitant and adjuvant temozolomide for glioblastoma", N Engl J Med 352:987-996 (2005).

Tamargo, et al, "Interstitial chemotherapy of the 9L gliosarcoma: controlled release polymers for drug delivery in the brain", Cancer Res. 53(2):329-333 (1993).

Valtonen, et al., "Interstitial chemotherapy with carmustine-loaded polymers for high-grade gliomas: a randomized double-blind study", Neurosurgery 41:44-48 (1997).

Wedge, et al., "In vitro evaluation of temozolomide combined with X-irradiation", Anticancer Drugs, 8:92-97 (1997).

West, "Drug delivery: pulsed polymers", Nat Mater., 2(11):709-10 (2003).

Westphal, et al., "A phase 3 trial of local chemotherapy with biodegradable carmustine (BCNU) wafers (Gliadel wafers) in patients with primary malignant glioma", Neuro Oncol 5:79-88 (2003).

Westphal, et al., "Gliadel wafer in initial surgery for malignant glioma: long-term follow-up of a multicenter controlled trial", Acta Neurochir (Wien), 148:269-275 (2006).

Wiestler, et al., "O6-alkylguanine-DNA alkyltransferase activity in human brain and brain tumors", Carcinogenesis, 5:121-124 (1984).

Yung, et al., "Multicenter phase II trial of temozolomide in patients with anaplastic astrocytoma or anaplastic oligoastrocytoma at first relapse. Temodal Brain Tumor Group" , J Clin Oncol ,17:2762-2771 (1999).

\* cited by examiner

COMBINATION OF LOCAL TEMOZOLOMIDE WITH LOCAL BCNU

CROSS REFERENCE TO RELATED APPLICATIONS

This application claims benefit of U.S. Provisional Application No. 61/355,828 filed Jun. 17, 2010, which is hereby incorporated herein by reference in its entirety.

STATEMENT REGARDING FEDERALLY SPONSORED RESEARCH OR DEVELOPMENT

This invention was made with Government Support under Agreement CA62474 awarded to Henry Brem by the National Institutes of Health—National Cooperative Drug Discovery/Development Groups.

FIELD OF THE INVENTION

This technology relates to formulations for chemotherapy, especially of brain tumors such as gliomas.

BACKGROUND OF THE INVENTION

New strategies are needed to improve the outcome of patients with adult glioblastoma multiforme (GBM). In addition to surgical resection (Rostomily et al. Baillieres Clin Neurol 5:345-369, 1996) and radiotherapy (Castro et al. Pharmacol Ther 98:71-108, 2003), numerous chemotherapeutic agents have been used to treat this disease (Parney et al. Cancer J 9:149-156, 2003), but limitations including poor central nervous system drug penetration and dose limiting toxicities have restricted their use (Rautioa et al. Curr Pharm Des 10:1341-1353, 2004). Temozolomide (TMZ), given orally as Temodar®, has been shown in randomized, placebo controlled, multi-institutional clinical trials, to be effective in prolonging survival and has received FDA approval for the treatment of newly diagnosed (Stupp et al. J Clin Oncol 20:1375-1382, 2002; Stupp et al. N Engl J Med 352:987-996, 2005) or recurrent (Yung et al. J Clin Oncol 17:2762-2771, 1999) malignant glioma. TMZ is an imidazotetrazine second-generation alkylating agent which, when given with radiation treatment has been shown to extend median survival 2.5 months compared to radiation alone (Stupp 2005) (Temodar® dose of 150-200 mg/m$^2$). Higher doses of Temodar®, which might increase efficacy, are associated with dose-limiting myelosuppression including severe leukopenia and thrombocytopenia (Stupp 2002, 2005; Yung 1999; Gerber et al. Neuro Oncol 9:47-52, 2007). Research efforts have been directed towards local delivery of agents to the site of the tumor to achieve maximal drug concentrations while limiting toxicity. Recent advances in the local delivery of chemotherapeutic agents have shown encouraging results in the treatment of patients with malignant gliomas. See Attenello 2008; Soffietti et al. Anticancer Drugs 18:621-632, 2007; Raza et al. Expert Opin Biol Ther 5:477-494, 2005. While a number of therapeutic clinical trials are currently underway, there continues to be a limited number of agents in the armamentarium to effectively combat this disease. Gliadel®, a biodegradable polymer containing the alkylating agent Carmustine (BCNU), is implanted locally into the surgical bed at the time of high grade glioma resection, and has been shown to increase survival in both newly diagnosed (Brem et al. J Neurooncol 26:111-123, 1995; Westphal et al. Neuro Oncol 5:79-88, 2003; Valtonen et al. Neurosurgery 41:44-48, 1997; Westphal et al. Acta Neurochir (Wien) 148:269-275, 2006) and recurrent (Brem et al. Lancet 345:1008-1012, 1995) malignant gliomas. Alkylating agents, such as BCNU and TMZ, have clearly shown effective dose-response cytotoxicity for many glioma cell lines in vitro (Raza 2005; Wedge Anticancer Drugs 8:92-97, 1997). The maximal doses for each drug, however, are limited due to dose dependent systemic toxicity. To this end, Gliadel® is used to maximize local concentrations of BCNU and minimize systemic exposure. Based on similar principles and on the fact that systemic toxicity has been observed as a dose limiting factor for TMZ (Stupp 2005; Gerber 2007; Brock et al. Cancer Res 58:4363-4348, 1998), it has been shown in rodents that intracranial delivery of TMZ has improved efficacy when compared to the systemic administration of TMZ (Brem 2007).

Recent clinical evidence has suggested that treatment with a combination of modalities consisting of surgical excision, locally delivered BCNU, concurrent and adjuvant systemic TMZ, and radiotherapy is safe and effective, and provides improved survival compared to each treatment group alone. See Menei 2008; McGirt 2010; La Rocca 2008; Gururangan et al. Neuro Oncol 3:246-250, 2001; Pan et al. J Neurooncol 88:353-357, 2008. These clinical advances in glioma therapy, with multimodality treatments, have led to an improvement in expected survival for GBM from 9 to 20 months (Menei "Biodegradable carmustine-impregnated wafers (Gliadel®): the French experience". Presented at the 8th Congress of the European Association of Neurooncology, Barcellona, Spain, Sep. 12-14, 2008; McGirt "Gliadel (BCNU) wafer plus concomitant temozolomide therapy after primary resection of glioblastoma multiforme" J Neurosurg (2010 in press); La Rocca "A phase 2 study of multi-modal therapy with surgery, carmustine (BCNU) wafer, radiation therapy (RT), and temozolomide (TMZ) in patients (pts) with newly diagnosed supratentorial malignant glioma (MG)" Presented at the 8th Congress of the European Association of Neurooncology, Barcellona, Spain, Sep. 12-14, 2008; Attenello et al. Ann Surg Oncol 15:2887-2893, 2008.

Although the survival time has increased from nine to twenty months, on average, there remains a critical need for even greater prolongation of survival, preferably while maintaining the best possible quality of life.

It is therefore an object of the present invention to provide compositions providing significantly great efficacy in treating tumors, with far fewer side effects that limit the dosage that can be used, and cause patient discomfort.

SUMMARY OF THE INVENTION

The additive effect of combined intracranial carmustine ("BCNU") with intracranial temozolomide ("TMZ"), and particularly in combination with radiation ("XRT"), in the treatment of two rat intracranial glioma models, the 9L gliosarcoma and the F98 glioma, demonstrates that local, preferably sustained, delivery of both drugs, especially in combination with radiation, is far more effective than delivery of either drug alone or one systemically and one locally, either with or without radiation. TMZ and BCNU were incorporated into biodegradable polymer discs that were implanted in F344 rats bearing established intracranial tumors useful as glioma models, the 9L gliosarcoma and the F98 glioma. In the 9L rodent glioma model, groups treated with the combination of local TMZ, local BCNU, and radiation (XRT) had 75% long-term survivors (LTS), which was superior to the combination of local TMZ and local BCNU (median survival of 95 days, LTS=25%) and the combination of oral TMZ, local BCNU and XRT (median survival of 62 days, LTS=12.5%).

In order to simulate the effect of this treatment in chemoresistant gliomas, a second rodent model was used with the F98 glioma, a cell line relatively resistant to alkylating agents due to expression of high levels of alkyltransferase, an enzyme that deactivates alkylating agents and is the major mechanism of resistance of gliomas. The triple therapy showed a significant improvement in survival when compared to controls ($p=0.0004$), local BCNU ($p=0.0043$), oral TMZ ($p=0.0026$), local TMZ ($p=0.0105$), and the combinations of either BCNU and XRT ($p=0.0378$) or oral TMZ and local BCNU ($p=0.0154$).

The survival of tumor-bearing animals in the 9L and F98 glioma models was improved with the local delivery of BCNU and TMZ, especially when combined with XRT, when compared with either treatment alone and with the clinically used modality of oral TMZ, local BCNU and XRT.

DETAILED DESCRIPTION OF THE INVENTION

I. Definitions

Figure 1:
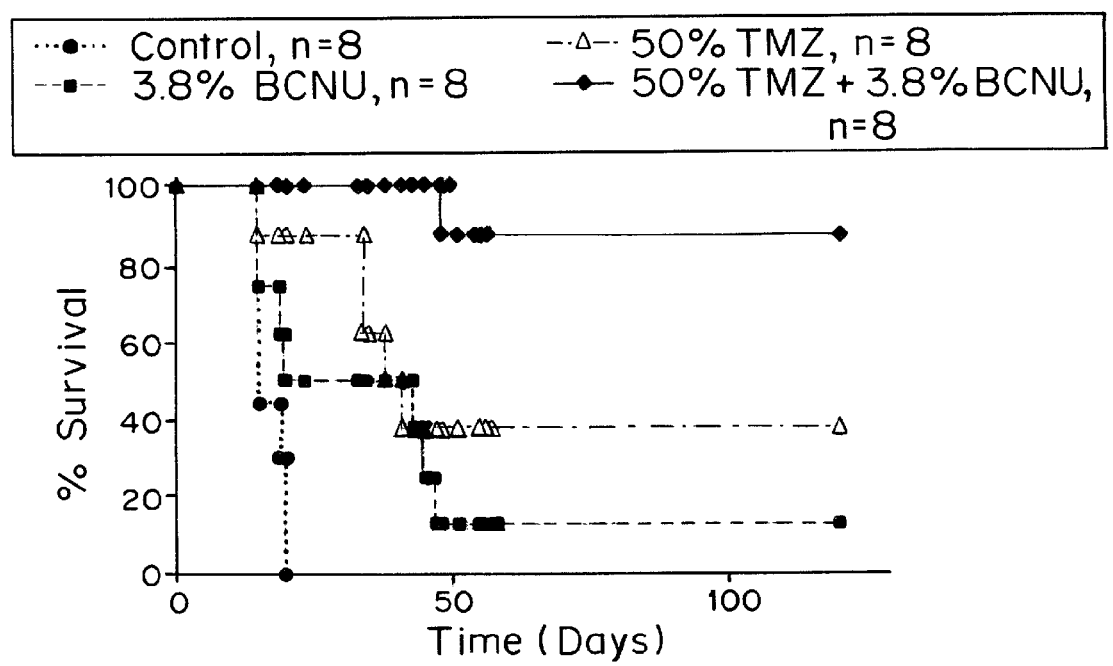
FIG. 1 is a Kaplan-Meier curve showing the efficacy (percent survival over time in days) of the combination of local BCNU and TMZ tested in the rat 9L gliosarcoma using F344 rats. The animals were divided into 4 groups and received either no treatment (dark circle, n=8), local BCNU (3.8%, dark square, n=8), local TMZ (50%, open triangle, n=8), or a combination of local BCNU and local TMZ (open diamond, 50% TMZ and 3.8% BCNU, n=8).

As used herein, radiation or "XRT" refers to radiation therapy as the application of radiation from an external radiation source.

As used herein, "local" therapy refers to therapy placed locally either surgically, via a needle or through a vessel or subcutaneously, or intramuscularly, or intraperitoneally.

As used herein, extended or sustained release refers to a therapeutically effective amount of active agent being released over a period of time ranging from weeks, months to years. Typically, release will be achieved over a period of one or more weeks following implantation.

As used herein, "a therapeutically effective amount" refers to a concentration of therapeutic agent capable of effecting a response.

As used herein, "efficacy" refers to affecting tumor size or prolonging survival As used herein, long term survival, LTS, is defined as animals alive 120 days after tumor implantation and in people who survive more than 9 months from original diagnosis.

II. Compositions

A. Chemotherapeutic Agents

Administration of two chemotherapeutics, temozolomide and BCNU (carmustine), locally has been demonstrated to provide greater than expected efficacy. These are typically provided in a polymeric matrix containing carmustine in a concentration range of 3.8-28% by weight and/or temozolomide in a concentration range of 40-70% by weight.

Other chemotherapeutic agents can be added to the combination. These typically include alkylating agents, nitrosoureas, and antimetabolites. Specific examples include 5FU, FUDR, cisplatin, carboplatin, doxorubicin, daunorubicins, cytoarabine, cyclophosphamide, paclitaxel, gemcitabine, ifosfamide, camptothecins such as irinotecan, methotrexate, procarbazine, vincristine, and vinblastin.

B. Formulations

Polymers

Microparticles, disks and wafers are formed from polymers, include soluble and water-insoluble, and biodegradable and nonbiodegradable polymers, including hydrogels, thermoplastics, and homopolymers, copolymers and blends of natural and synthetic polymers. Most preferred polymers are polyanhydrides and polyhydroxy acids, especially poly(lactic acid-glycolic acid) copolymers. These can be selected to provide optimal incorporation and release of drug.

In the preferred embodiment, the polymer is a biodegradable polyanhydride copolymer, poly[bis(p-carboxyphenoxy)propane:sebacic acid] in a 20:80 molar ratio.

Representative natural polymers which can be used include proteins, such as zein, modified zein, casein, gelatin, gluten, serum albumin, or collagen, and polysaccharides such as dextrans, polyhyaluronic acid, alginic acid, and poly(amino) acids. Celluloses also can be used. As defined herein the term "celluloses" includes naturally occurring and synthetic celluloses, such as alkyl celluloses, cellulose ethers, cellulose esters, hydroxyalkyl celluloses and nitrocelluloses. Exemplary celluloses include ethyl cellulose, methyl cellulose, carboxymethyl cellulose, hydroxymethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, cellulose triacetate and cellulose sulfate sodium salt. Chitin, chitosan and other similar materials can be used.

Representative synthetic polymers which can be used include hydrophilic polymers, such as those containing carboxylic groups, including polyacrylic acid, and hydrophobic polymers such as the bioerodible polymers including polyanhydrides, poly(hydroxy acids) and polyesters, as well as blends and copolymers thereof. Representative bioerodible poly(hydroxy acids) and copolymers thereof which can be used include poly(lactic acid), poly(glycolic acid), poly(hydroxy-butyric acid), poly(hydroxyvaleric acid), poly(caprolactone), poly(lactide-co-caprolactone), poly(lactide-co-glycolide, polyanhydrides and polyorthoesters, can be used.

Additional synthetic polymers include polyphosphazenes, polyamides, polycarbonates, polyacrylamides, polysiloxanes, polyurethanes and copolymers thereof.

Polymers of acrylic and methacrylic acids or esters and copolymers thereof include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other polymers which can be used include polyalkylenes such as polyethylene and polypropylene; polyarylalkylenes such as polystyrene; poly(alkylene glycols), such as poly(ethylene glycol); poly(alkylene oxides), such as poly(ethylene oxide); and poly(alkylene terephthalates), such as poly(ethylene terephthalate). Additionally, polyvinyl polymers can be used, which, as defined herein includes polyvinyl alcohols, polyvinyl ethers, polyvinyl esters and polyvinyl halides. Exemplary polyvinyl polymers include poly(vinyl acetate), polyvinyl phenol and polyvinylpyrrolidone.

Polymers which alter viscosity as a function of temperature or shear or other physical forces also may be used. Poly(oxyalkylene) polymers and copolymers such as poly(ethylene oxide)-polypropylene oxide) (PEO-PPO) or poly(ethylene oxide)-poly(butylene oxide) (PEO-PBO) copolymers, and copolymers and blends of these polymers with polymers such as poly(alpha-hydroxy acids), including but not limited to lactic, glycolic and hydroxybutyric acids, polycaprolactones, and polyvalerolactones, can be synthesized or commercially obtained.

These polymers can be obtained from sources such as Sigma Chemical Co., St. Louis, Mo.: Polysciences, Warrenton, Pa.; Aldrich, Milwaukee, Wis.; Fluka, Ronkonkoma, N.Y.; and BioRad, Richmond, Calif., or can be synthesized from monomers obtained from these or other suppliers using standard techniques.

C. Methods of Manufacture

The formulations are preferably polymeric in the form of wafers, disks or microparticles (microspheres, microparticles, microcapsules, or nanoparticles).

i. Methods of Making Polymeric Wafers or Disks

In the preferred embodiment, the drug is homogeneously dispersed in a wafer approximately 1.45 cm in diameter and 1 mm thick. In the FDA approved product, GLIADEL®, 192.3 mg of BCNU is homogenously dispersed throughout the polymer matrix. Typically polymer is dissolved in an FDA approved solvent such as methylene chloride, drug added to a desired weight percentage typically between 10 and 90% by weight, more typically between 40 and 70%, and most preferably about 50%, and the product spray dried to solvent cast to form polymeric implants. Solvent is removed by evaporation, and the resulting implants sealed under nitrogen or another inert gas into a foil or light resistant blister pack.

ii. Methods of Making Microparticles

Generally, microspheres have a diameter from the nanometer range up to about 300 microns, most preferably 40-80 microns. The microparticles must have both structural integrity and optimal surface area, including both a crenulated outer surface and a highly porous or trabeculated interior. Porosity of the interior is designed so that internal voids are interconnected to each other and to the microsphere surface prior to injection in the body.

In one embodiment, the microspheres can be fabricated using methods including solvent evaporation, hot-melt microencapsulation or spray drying. Microparticles made of thermoplastic polymers such as polyanhydrides made of bis-carboxyphenoxypropane and sebacic acid or poly(fumaric-co-sebacic) can be prepared by hot-melt or solvent evaporation microencapsulation. Polystyrene and polyhydroxy acid microspheres can be prepared by solvent evaporation. Hydrogel microspheres can be prepared by dripping a polymer solution, such as alginate, chitosan, alginate/polyethylenimine (PEI) and carboxymethyl cellulose (CMC), from a reservoir though microdroplet forming device into a stirred ionic bath, as disclosed in WO 93/21906.

a. Solvent Evaporation

Methods for forming microspheres using solvent evaporation techniques are described in E. Mathiowitz et al., J. Scanning Microscopy, 4:329 (1990); L. R. Beck et al., Feral. Steril., 31:545 (1979); and S. Benita et al., J. Pharm. Sci., 73:1721 (1984), the disclosures of which are incorporated herein by reference. The polymer is dissolved in a volatile organic solvent, such as methylene chloride. A substance to be incorporated is added to the solution, and the mixture is suspended in an aqueous solution that contains a surface active agent such as poly(vinyl alcohol). The resulting emulsion is stirred until most of the organic solvent evaporated, leaving solid microspheres. Microspheres with different sizes (1-1000 microns) and morphologies can be obtained by this method. This method is useful for relatively stable polymers like polyesters and polystyrene. However, labile polymers, such as polyanhydrides, may degrade during the fabrication process due to the presence of water. For these polymers, some of the following methods performed in completely anhydrous organic solvents are more useful.

b. Hot Melt Microencapsulation

Microspheres can be formed from polymers such as polyesters and polyanhydrides using hot melt microencapsulation methods as described in Mathiowitz et al., Reactive Polymers, 6:275 (1987), the disclosure of which is incorporated herein by reference. In this method, the use of polymers with molecular weights between 3-75,000 daltons is preferred. In this method, the polymer first is melted and then mixed with the solid particles of a substance to be incorporated that have been sieved to less than 50 microns. The mixture is suspended in a non-miscible solvent (like silicon oil), and, with continuous stirring, heated to 5° C. above the melting point of the polymer. Once the emulsion is stabilized, it is cooled until the polymer particles solidify. The resulting microspheres are washed by decantation with petroleum ether to give a free-flowing powder. Microspheres with sizes between one to 1000 microns are obtained with this method.

c. Solvent Extraction

This technique is described, for example, in PCT WO 93/21906. The substance to be incorporated is dispersed or dissolved in a solution of the selected polymer in a volatile organic solvent like methylene chloride. This mixture is suspended by stirring in an organic oil, such as silicon oil, to form an emulsion. Microspheres that range between 1-300 microns can be obtained by this procedure.

d. Spray-Drying

Methods for forming microspheres using spray drying techniques are described in U.S. Pat. No. 6,262,034. The polymer is dissolved in an organic solvent such as methylene chloride. A known amount of a substance to be incorporated is suspended (insoluble agent) or co-dissolved (soluble agent) in the polymer solution. The solution or the dispersion then is spray-dried. Microspheres typically ranging between 1-10 microns are obtained.

e. Phase Inversion

Microspheres can be formed from polymers using a phase inversion method wherein a polymer is dissolved in a good solvent, fine particles of a substance to be incorporated, such as a drug, are mixed or dissolved in the polymer solution, and the mixture is poured into a strong non-solvent for the polymer, to spontaneously produce, under favorable conditions, polymeric microspheres, wherein the polymer is either coated on the particles or the particles are dispersed in the polymer. The method can be used to produce microparticles in a wide range of sizes, including, for example, about 100 nanometers to about 10 microns. Exemplary polymers which can be used include polyvinylphenol and polylactic acid. Substances which can be incorporated include, for example, imaging agents such as fluorescent dyes, or biologically active molecules such as proteins or nucleic acids.

f. Protein Microencapsulation

Protein microspheres can be formed by phase separation in a non-solvent followed by solvent removal as described in U.S. Pat. No. 5,271,961 to Mathiowitz et al. Proteins which can be used include prolamines such as zein. Additionally, mixtures of proteins or a mixture of proteins and a bioerodable polymeric material such as a polylactide can be used. In one embodiment, a prolamine solution and a substance to be incorporated are contacted with a second liquid of limited miscibility with the proline solvent, and the mixture is agitated to form a dispersion. The prolamine solvent then is removed to produce stable prolamine microspheres without crosslinking or heat denaturation. Other prolamines which can be used include gliadin, hordein and kafirin. Substances which can be incorporated in the microspheres include, in addition to the metal compound, pharmaceuticals, pesticides, nutrients and imaging agents. Other proteins include albumin and collagen.

g. Low Temperature Casting of Microspheres

Methods for very low temperature casting of controlled release microspheres are described in U.S. Pat. No. 5,019,400 to Gombotz et al. A polymer is dissolved in a solvent together with a dissolved or dispersed substance to be incorporated, and the mixture is atomized into a vessel containing a liquid non-solvent at a temperature below the freezing point of the polymer-substance solution, which freezes the polymer droplets. As the droplets and non-solvent for the polymer are warmed, the solvent in the droplets thaws and is extracted into the non-solvent, resulting in the hardening of the microspheres.

h. Double Walled Microcapsules

In one embodiment of a method for preparing multiwall polymer microspheres, two hydrophilic polymers are dissolved in an aqueous solution. A substance to be incorporated is dispersed or dissolved in the polymer solution, and the mixture is suspended in a continuous phase. The solvent then is slowly evaporated, creating microspheres with an inner core formed by one polymer and an outer layer of the second polymer. The continuous phase can be either an organic oil, a volatile organic solvent, or an aqueous solution containing a third polymer that is not soluble with the first mixture of polymers and which will cause phase separation of the first two polymers as the mixture is stirred.

Multilayer polymeric delivery devices can be prepared from two or more hydrophilic polymers using the method. Any two or more different biodegradable, or non-degradable, water soluble polymers which are not soluble in each other at a particular concentration as dictated by their phase diagrams may be used. Microspheres containing a polymeric core made of a first polymer and a uniform coating of a second polymer, and a substance incorporated into at least one of the polymers, can be made as described in U.S. Pat. No. 4,861,627.

i. Hydrogel Microspheres

Microspheres made of gel-type polymers, such as alginate, are produced through traditional ionic gelation techniques. The polymer first is dissolved in an aqueous solution, mixed with a substance to be incorporated, and then extruded through a microdroplet forming device, which in some instances employs a flow of nitrogen gas to break off the droplet. A slowly stirred ionic hardening bath is positioned below the extruding device to catch the forming microdroplets. The microspheres are left to incubate in the bath for twenty to thirty minutes in order to allow sufficient time for gelation to occur. Microsphere particle size is controlled by using various size extruders or varying either the nitrogen gas or polymer solution flow rates.

Chitosan microspheres can be prepared by dissolving the polymer in acidic solution and crosslinking it with tripolyphosphate. Carboxymethyl cellulose (CMC) microspheres can be prepared by dissolving the polymer in acid solution and precipitating the microsphere with lead ions. Alginate/polyethylene imide (PEI) can be prepared in order to reduce the amount of carboxylic groups on the alginate microcapsule. The advantage of these systems is the ability to further modify their surface properties by the use of different chemistries. In the case of negatively charged polymers (e.g., alginate, CMC), positively charged ligands (e.g., polylysine, polyethyleneimine) of different molecular weights can be ionically attached.

Examples of methods of making such particles are described in U.S. Pat. Nos. 7,175,912, 7,175,909, and U.S. Patent Publication 2005/0271745.

iii. Implantable Microchips

Polymeric microchips for multi-dose delivery are described by Richards, et al., Nat. Mater. (2003) 2(11):709-10 and Kim, et al. J Control Release. (2007) 123(2):172-8. Biodegradable polymeric microchips can be fabricated as described in these studies for release of active over an extended period, for example, 142 day. As described in these papers, the microchips were 1.2 cm in diameter, 480-560 microm thick and had 36 reservoirs that could each be filled with a different chemical. The devices were fabricated from poly(L-lactic acid) and had poly(D,L-lactic-co-glycolic acid) membranes of different molecular masses covering the reservoirs. A drug delivery system can be designed with the potential to release pulses of different drugs at intervals after implantation in a patient by using different molecular masses or materials for the membrane. The devices can also be designed to have differential degradation rates in vivo and in vitro, using different polymer composition and/or molecular weights, such as biocompatible poly(lactic acid) and poly (glycolic acid) homo- and co-polymers for a polymeric drug-delivery microchip.

Microchips for controlled and/or staggered or stimulus driven release are available from MicroChips Technology, MA. See also U.S. Pat. Nos. 6,491,666, 6,527,762, 6,976, 982, 7,226,442, and 7,604,628.

III. Methods of Treatment

A. Conditions to be Treated

The polymeric implants are used preferably for the treatment of GBM although they may be used to treat other types of tumors, especially brain tumors, most preferably following surgical resection.

B. Dosages and Administration Regimes

The effective dosages can be determined by those skilled in the art based on the known pharmacokinetics of the drugs, prior studies using Glialdel®, and animal studies such as those described herein.

In a preferred embodiment, the patient is also treated using standard techniques for radiation treatment of cancer patients, especially those with GBM. See, for example, Chang, et al., JAMA 293(20):557-564 (2005); Raza, et al. Expert Opin. Biol. Ther. 5(4):477-494 (2005), and Castro, et al. Pharmacol. Ther. 98(1):71-108 (2003).

The present invention will be further understood by reference to the following comparative examples.

EXAMPLE 1

Combination of Intracranial Temozolomide with Intracranial Carmustine in a Rodent Glioma Model Materials and Methods Polymer Formation TMZ, provided by the National Institute of Health/National Cancer Institute, (Bethesda, Md.), was incorporated into a polyanhydride CPP:SA 20:80 polymer at concentrations of 50% (w/w) by methods as described by Tamargo, et al., Cancer Res. 53(2):329-333 (1993). BCNU was purchased from the Johns Hopkins Hospital pharmacy (Bristol Meyers; Princeton, N.J.) and polymers were made at concentrations of 3.8% (w/w) in a similar fashion. The polymers were then pressed into discs weighing approximately 10 mg. Blank polymers (100% CPP:SA) were made in an analogous manner. In vitro release kinetics, biodistribution studies, and studies to determine maximally tolerated dose of BCNU and TMZ polymers as described by Brem, et al., Cancer Chemother. Pharmacol. 60(5):643-650 (2007); Tamargo, et al., Cancer Res. 53(2):329-333 (1993); and Grossman, et al., J. Neurosurg. 76(4):640-647 (1992). Polymers were stored at −20° C. until use.

Tumor Cells

The 9L gliosarcoma was obtained from Dr. M. Barker at the University of California-San Francisco Brain Tumor Research Center (San Francisco, Calif.). For tumor piece implantation, 9L tumor pieces measuring 2 $mm^3$ were passaged in the flank of F344 rats (female, 150 to 200 g) every 3 to 4 weeks. For intracranial implantation, the 9L gliosarcoma tumor was surgically excised from the carrier animal, cut into 1 $mm^3$ pieces and placed in sterile 0.9% NaCl on ice. The F98 glioma was obtained from Dr. R. Barth (Ohio State University, Columbus, Ohio). Tumor cells were maintained in DMEM culture medium (Invivogen, San Diego, Calif.) containing 10% fetal bovine serum in humidified incubators.

Animals

F344 female rats weighing 150 to 200 g, purchased from Harlan Bioproducts, Indianapolis, Ind., were used. They were housed in standard facilities and given free access to food and water. All animals were treated in accordance with the policies and guidelines of the Johns Hopkins University Animal Care and Use Committee.

Anesthesia

Rats were anesthetized with an intraperitoneal injection of 0.6 mL of a stock solution containing ketamine hydrochloride (75 mg/kg) (100 mg/mL; ketamine HCl), xylazine (7.5 mg/kg) (100 mg/mL), and ethanol (14.25%) in a sterile 0.9% NaCl solution.

Intracranial Glioma Model

For intracranial implantation of the 9L gliosarcoma, 127 (32 for the first and 95 for the second experiment) F344 female rats were anesthetized. The head was shaved with clippers and prepared with alcohol and prepodyne solution. A midline scalp incision was made, exposing the sagittal and coronal sutures. Using an electric drill with a 2 mm round cutting burr, a small hole was made in the skull centered 3 mm lateral to the sagittal suture, and 5 mm posterior to the coronal suture. Care was taken to avoid the sagittal sinus. Forceps were used to lift off the remaining bone. Under microscopic magnification, a dural opening and then cortical opening were made. A small area of cortex and white matter was resected, and, once hemostasis was achieved, a single tumor piece was placed in the resection cavity. The skin was then closed with surgical staples.

For intracranial tumor injection of the F98 glioma cells, 85 F344 female rats were anesthetized. The procedure was similar to the 9L implant however after the burr hole was drilled, the animals were then placed in a stereotactic frame and $1 \times 10^5$ F98 glioma cells were injected over 3 min via a 26-gauge needle inserted to a depth of 4 mm at the center of the burr hole. After tumor cell inoculation, the needle was removed, the site was irrigated with normal saline, and the incision was closed with surgical staples.

Radiation Therapy (XRT)

For XRT, animals were anesthetized, placed at a fixed distance from the radiation source and shielded with a square primary collimator (1 cm in diameter) centered over the tumor implantation site. The radiated animals received external beam single-dose radiation treatment by using a 138Cs laboratory irradiator (Mark 1 Irradiator, Model 68) at a dose of 20 Gy.

Efficacy Studies of Local TMZ Given in Combination with Local BCNU in 9L Gliosarcoma To determine the efficacy of the combination of locally delivered TMZ with locally delivered BCNU, the tumor-bearing rats were randomized into groups of eight for treatment on post-operative Day 5. The animals received either no treatment (control), 3.8% BCNU polymer locally (total dose 0.38 mg BCNU), 50% TMZ polymer locally (total dose 5 mg TMZ), or both 3.8% BCNU and 50% TMZ polymers locally. Animals were observed for neurological and systemic toxicity, and survival was recorded. Any animals appearing moribund were sacrificed and date of death was recorded. At Day 120, all surviving rats were deemed long-term survivors (LTS) and were euthanized. Histopathological studies of all animals' brains harvested at time of death or euthanasia were examined to confirm the presence or absence of tumor.

Efficacy Studies of Local TMZ Given in Combination with Local BCNU and XRT in 9L Gliosarcoma and F98 Glioma To determine the efficacy of the combination of locally delivered TMZ with locally delivered BCNU and XRT, tumor-bearing rats were randomized into groups of sixteen for treatment on post-operative Day 5. Animals received either no treatment (controls), 3.8% BCNU polymer locally, 50% TMZ polymer locally, or both 3.8% BCNU and 50% TMZ polymers locally. On the same day half of the animals in each group received XRT. Animals were observed for neurological and systemic toxicity, and survival was recorded. Any animals appearing moribund were sacrificed and date of death recorded. At Day 120, all surviving rats were deemed LTS, however, the experiment was allowed to continue to 150 days because the treatment animals looked healthy. Histopathological studies of all animals' brains harvested at time of death or euthanasia were examined to confirm the presence or absence of tumor.

Statistical Analysis

For all efficacy studies, death was the primary end-point. The distribution of the intervals until death was determined by the method of Kaplan and Meier. Statistical analysis was completed using the GraphPad Prism 4 software.

Results

In Vivo Efficacy of Locally Delivered TMZ And BCNU Against 9L Gliosarcoma

Intracranial delivery of combined TMZ and BCNU polymers increased median survival and produced more LTS when compared to the control group and either treatment option given alone. (Table 1 and FIG. 1) Control animals had a median survival of 15 days. Animals treated with BCNU or TMZ alone had statistically improved survival as compared to controls, with a median survival of 20 days (p=0.0435) and 38 days (p=0.0009), respectively. The BCNU treatment group yielded 12.5% LTS while the TMZ group had 37.5% LTS. There was no statistical difference between the two individual treatment groups (p=0.1635). Animals treated with the combination of intracranial BCNU and TMZ had the longest prolongation of survival, 87.5% of the animals surviving longer than 120 days (median survival was not reached). Survival was significantly greater in this combination group as compared to the control group (p<0.0001), the group that received BCNU alone (p=0.0018), and the group that received TMZ alone (p=0.0433) alone. Histopathological review of the LTS revealed no evidence of tumor burden upon completion of the study. Histopathological review of the animals that died earlier, demonstrated the existence of tumor as the cause of death. No evidence of systemic toxicity was observed.

TABLE 1

Treatment of the 9L experimental malignant glioma model with locally delivered TMZ and BCNU

| Group | Median survival (days) | Long-term survivors (%) | P-values |
| --- | --- | --- | --- |
| Control (n = 8) | 15 (15-20) | 0 | |
| 3.8% BCNU polymer (n = 8) | 20 (15-120) | 12.5 | = 0.0435 vs. controls<br>= 0.1635 vs. 50% TMZ |
| 50% TMZ polymer (n = 8) | 38 (15-120) | 37.5 | = 0.0009 vs. controls<br>= 0.1635 vs. 3.8% BCNU |
| 3.8% BCNU polymer + 50% TMZ polymer (n = 8) | Median not reached | 87.5 | <0.0001 vs. controls<br>= 0.0018 vs. 3.8% BCNU<br>= 0.0433 vs. 50% TMZ |

Figure 2A:
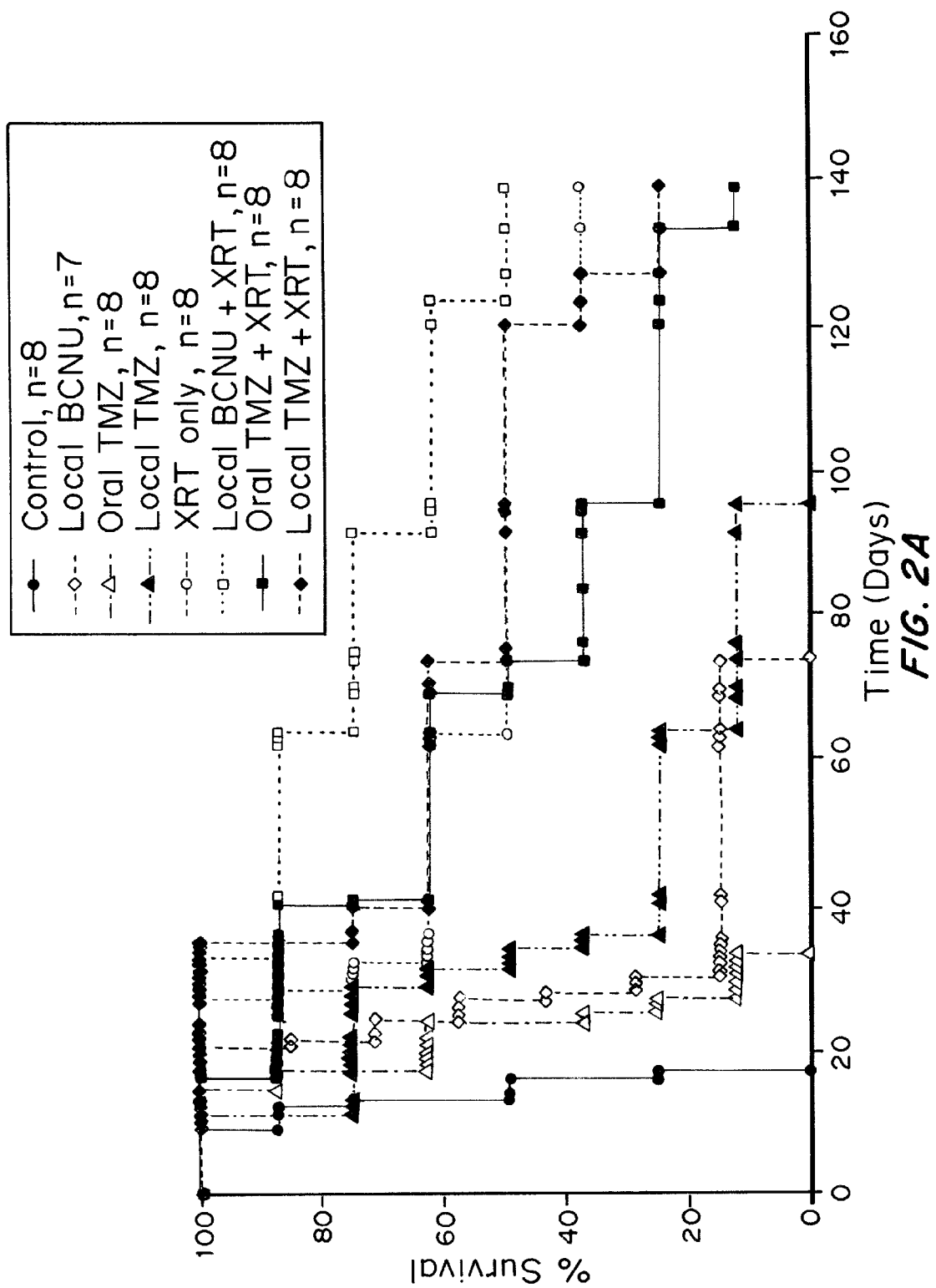
FIGS. 2A and 2B are Kaplan-Meier curves showing the efficacy (percent survival over time in days) of the combination of local BCNU, local TMZ and XRT in the rat 9L gliosarcoma using F344 rats. The animals were divided into 12 groups and received either no treatment (dark circle, n=8; 2A and 2B), local BCNU (open diamond, n=7, 2A), local TMZ (dark triangle, n=8, 2A), XRT only (open circle, n=8, 2A), local BCNU and local TMZ combined (shaded circle, n=8, 2B), oral TMZ (shaded triangle, n=8, 2A), oral TMZ and local BCNU (dark triangle, n=8, 2B), local BCNU and XRT open triangle, n-8, 2A), local TMZ and XRT open diamond, n=8, 2A), local BCNU and local TMZ combined with XRT (dark square, n=8, 2B), oral TMZ and XRT (shaded triangle, n=8, 2A), or oral TMZ and local BCNU combined with XRT (shaded square, n=8, 2B).
Figure 2B:
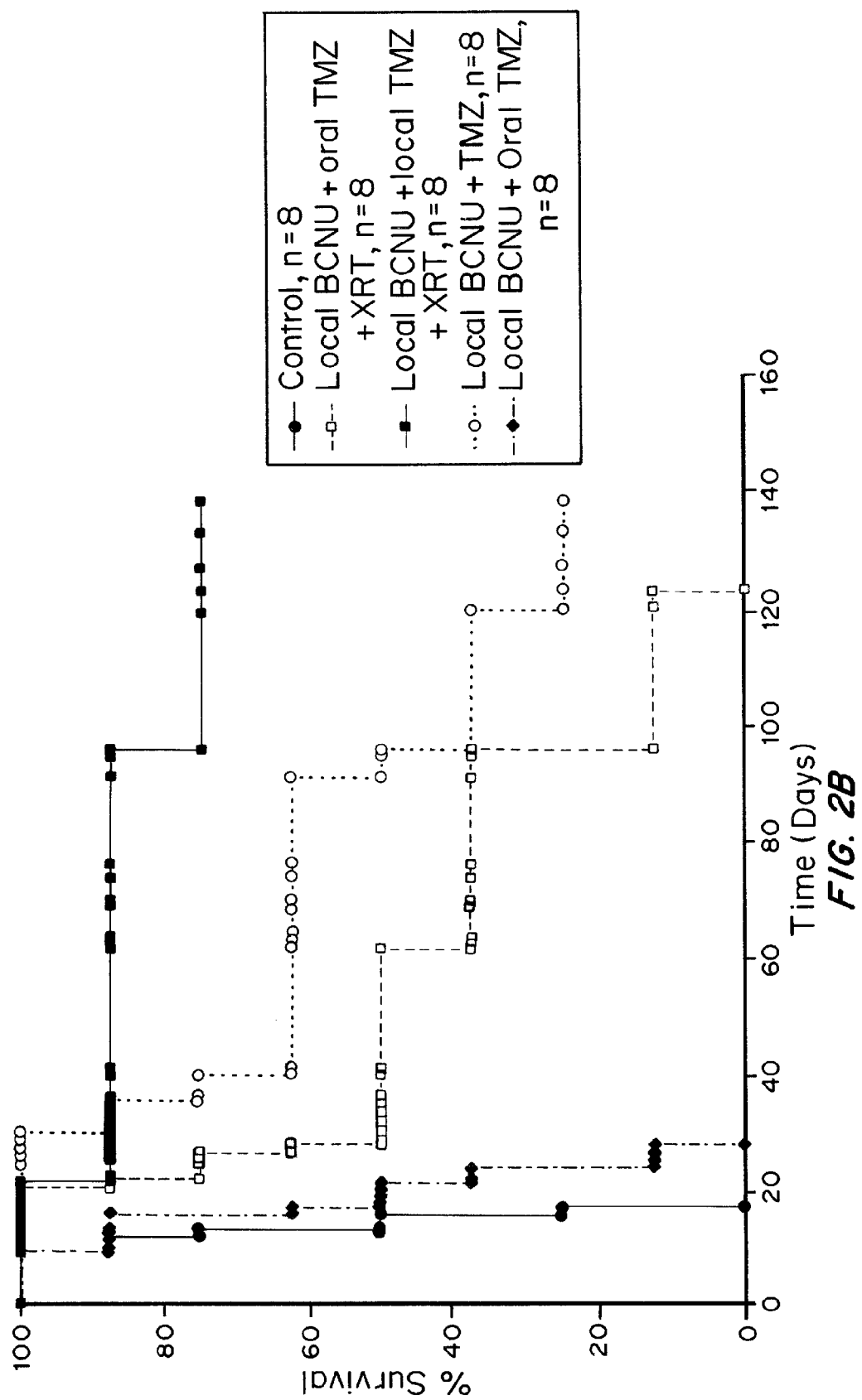

In Vivo Efficacy of Locally Delivered TMZ and BCNU with XRT Against 9L Gliosarcoma Intracranial delivery of TMZ and BCNU polymers in combination with XRT increased median survival and produced more LTS when compared to the control group or either treatment option alone (Table 2 and FIGS. 2A and 2B). Control animals had a median survival of 16 days. Animals treated with local BCNU and local TMZ had improved survival compared to controls (p<0.0001) and either treatment alone (BCNU-p=0.0018, TMZ-p=0.0158), with a median survival of 95 days and 25% LTS. The addition of XRT in this treatment group resulted in the longest prolongation of survival with median survival not reached and 75% of the animals surviving greater than 120 days. Survival was greater in the combination group with XRT than either the control group (p<0.0001), or the combination of local BCNU and local TMZ (p=0.0652). The combination of the three treatment modalities showed a clear trend towards superiority over the simultaneous local delivery of BCNU and TMZ but did not reach the level of statistical significance. However, the indices of survival with the latter option (median survival=95 days, LTS=25%) are clearly inferior to the triple therapy (median survival not reached, LTS=75%). XRT was not statistically different from the triple combination treatment group, with a median survival of 74 days, and 37.5% LTS. However, median survival was not reached and there were more LTS in the triple combination therapy group. In addition, the combination scheme provides a greater survival benefit than the clinically used combination of local BCNU, oral TMZ and XRT (median survival=62 days, LTS=12.5%, p=0.0033). Histopathological review of the LTS revealed no evidence of tumor burden upon completion of the study. Histopathological review of the animals that died earlier, demonstrated the existence of tumor as the cause of death. No evidence of systemic toxicity was observed with our proposed treatment.

TABLE 2

Treatment of the 9L experimental glioma model with locally delivered TMZ and BCNU and XRT

| Group | Median survival (days) | Long-term survivors (%) | P-values |
| --- | --- | --- | --- |
| Control (n = 8) | 16 (9-17) | 0 | |
| 50 mg/kg oral TMZ (n = 8) | 24 (14-33) | 0 | = 0.003 vs. controls<br>= 0.0322 vs. local TMZ |
| 3.8% BCNU polymer (n = 7) | 27 (20-74) | 0 | = 0.0002 vs. controls<br>= 0.0018 vs. local TMZ and local BCNU |
| 50% TMZ polymer (n = 8) | 34 (11-95) | 0 | = 0.0113 vs. controls<br>= 0.0158 vs. local TMZ and local BCNU |

TABLE 1-continued

Treatment of the 9L experimental malignant glioma model with locally delivered TMZ and BCNU

| Group | Median survival (days) | Long-term survivors (%) | P-values |
| --- | --- | --- | --- |
| TMZ polymer (n = 8) | (48-120) | | BCNU<br>= 0.0433 vs. 50% TMZ |

TABLE 2-continued

Treatment of the 9L experimental glioma model with locally delivered TMZ and BCNU and XRT

| Group | Median survival (days) | Long-term survivors (%) | P-values |
|---|---|---|---|
| XRT (20Gy) (n = 8) | 74 (27-120) | 37.5 | <0.0001 vs. controls |
| 3.8% BCNU polymer + XRT (n = 8) | (33-120) | 50 | = 0.0004 vs. controls<br>= 0.0004 vs. local BCNU |
| 50% TMZ polymer + XRT (n = 8) | 120 (35-120) | 25 | <0.0001 vs. controls<br>= 0.0091 vs. local TMZ |
| 3.8% BCNU polymer + 50 mg/kg oral TMZ (n = 8) | 21 (9-28) | 0 | = 0.0287 vs. controls<br>= 0.054 vs. local BCNU<br>= 0.3107 vs. oral TMZ |
| 3.8% BCNU polymer + 50 mg/kg oral TMZ + XRT (n = 8) | 62 (20-120) | 12.5 | <0.0001 vs. controls<br>= 0.1486 vs. BCNU<br>= 0.0234 vs. oral TMZ<br>= 0.1428 vs. XRT |
| 3.8% BCNU polymer + 50% TMZ polymer (n = 8) | 95 (29-120) | 25 | <0.0001 vs. controls<br>= 0.0018 vs. local BCNU<br>= 0.0158 vs. local TMZ |
| 3.8% BCNU polymer + 50% TMZ polymer + XRT (n = 8) | Median not reached (21-120) | 75 | <0.0001 vs. controls<br>= 0.001 vs. local BCNU<br>= 0.0007 vs. local TMZ<br>= 0.1378 vs. XRT |

In Vivo Efficacy of BCNU and TMZ with XRT in F98 Glioma

Figure 3A:
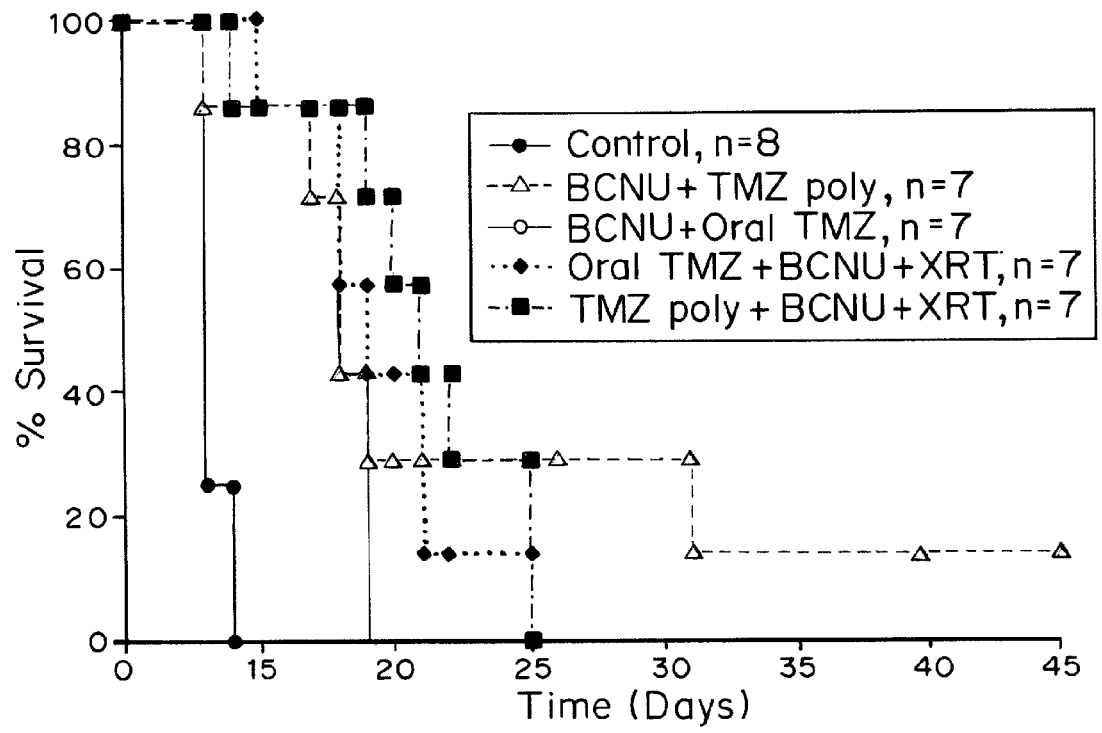
FIGS. 3A, 3B, and 3C are Kaplan-Meier curves showing the efficacy (percent survival over time in days) of the combination of local BCNU, local TMZ and XRT tested in the rat F98 glioma, which is resistant to alkylating agents, using F344 rats. The animals were divided into 12 groups and received either no treatment (dark circle, n=8, 3A, 3B, 3C), local BCNU (dark square, n=7, 3C), local TMZ (open diamond, n=6, 3C), local BCNU and local TMZ combined (open triangle, n=8, 3A), oral TMZ (dark diamond, n=8, 3C), oral TMZ and local BCNU (shaded circle, n=7, 3A), local BCNU and XRT dark diamond, n=8, 3B), local TMZ and XRT (open square, n=7, 3B), local BCNU and local TMZ combined with XRT (open square, n=7, 3A), oral TMZ and XRT (shaded diamond, n=8, 3B), or oral TMZ and local BCNU combined with XRT (dark diamond, n=7, 3A).
Figure 3B:
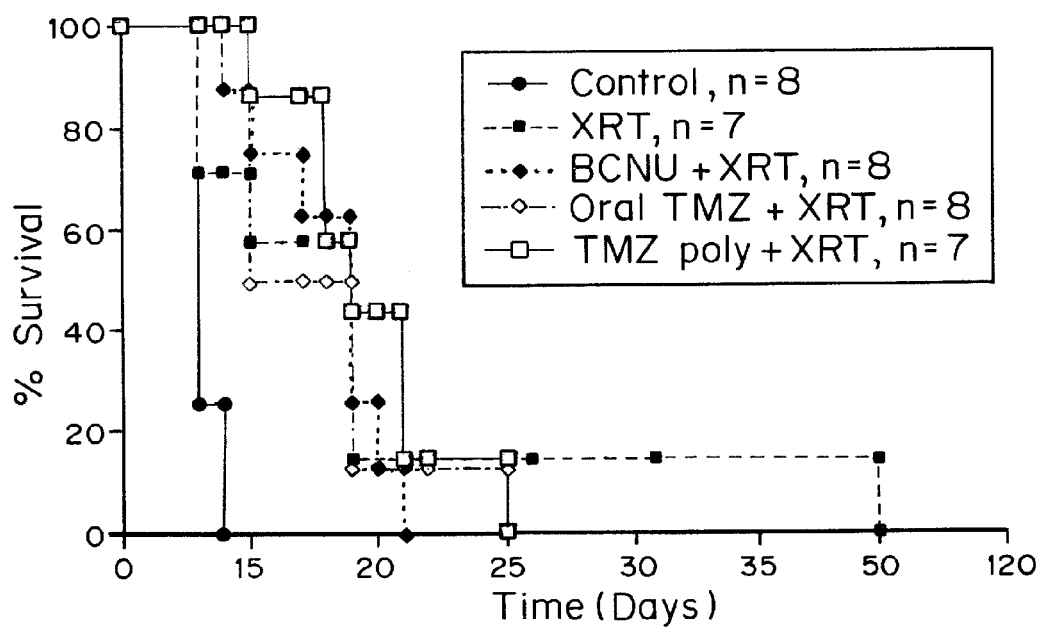
Figure 3C:
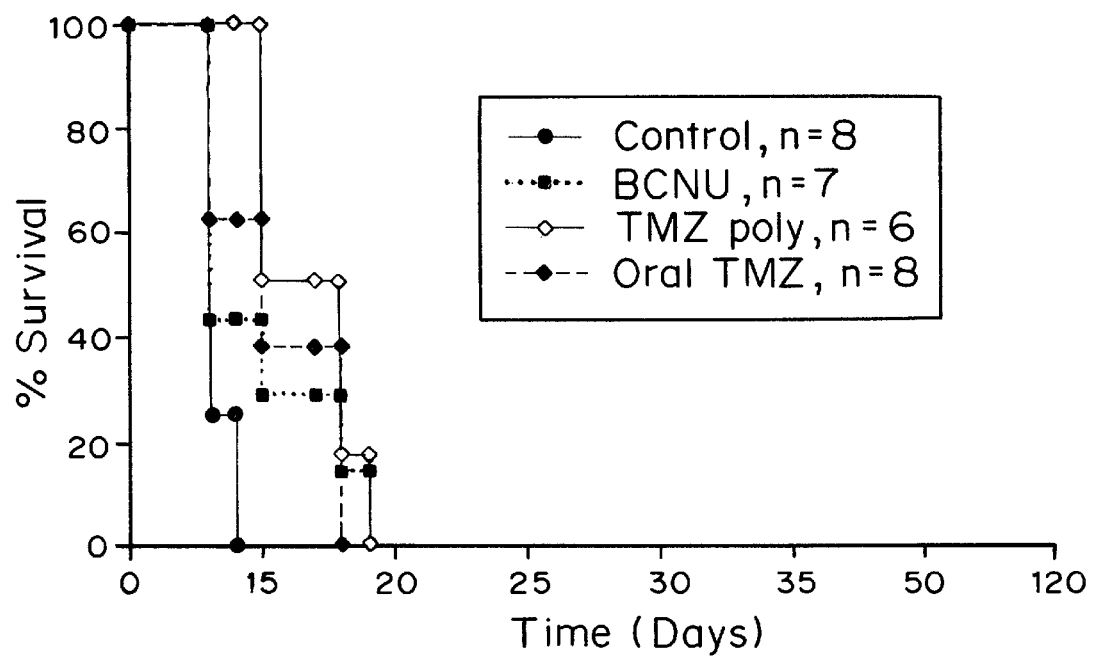

Intracranial delivery of combined TMZ and BCNU polymers in combination with external radiation increased median survival when compared to the control group or either treatment option alone (Table 3, FIGS. 3A, 3B, and 3C). Control animals had a median survival of 13 days. Animals treated with local BCNU combined with local TMZ and radiation had improved survival compared to controls (p=0.0004) and to either local BCNU (p=0.0043) or local TMZ (p=0.0105), with a median survival of 21 days. At the same time this scheme showed significantly better results when compared with the administration of local BCNU and radiation (p=0.0378) or local BCNU and oral TMZ (p=0.0154). The combined local delivery of BCNU and TMZ was superior to the administration of oral TMZ (p=0.0492). There were no long-term survivors in any of the groups. No evidence of systemic toxicity was observed with the treatment.

TABLE 3

Treatment of the F98 experimental glioma model with locally delivered TMZ and BCNU and XRT

| Group | Median survival (days) | Long-term survivors (%) | P-values |
|---|---|---|---|
| Control (n = 8) | 13 (13-14) | 0 | |
| 50 mg/kg oral TMZ (n = 8) | 15 (13-18) | 0 | = 0.013 vs. controls<br>= 0.2339 vs. local TMZ |
| 3.8% BCNU polymer (n = 7) | 13 (13-19) | 0 | = 0.0949 vs. controls<br>= 0.1269 vs. local TMZ and local BCNU |
| 50% TMZ polymer (n = 6) | 15 (15-19) | 0 | = 0.0002 vs. controls<br>= 0.0492 vs. local TMZ and local BCNU |
| XRT (20Gy) (n = 7) | 19 (13-48) | 0 | = 0.0062 vs. controls |
| 3.8% BCNU polymer + XRT (n = 8) | 19 (14-21) | 0 | = 0.0002 vs. controls<br>= 0.05 vs. local BCNU<br>= 0.0218 vs. oral TMZ |
| 50% TMZ polymer + XRT (n = 7) | 19 (15-25) | 0 | = 0.0001 vs. controls<br>= 0.05 vs. local TMZ<br>= 0.0093 v. oral TMZ |
| 3.8% BCNU polymer + 50 mg/kg oral TMZ (n = 7) | 18 (15-19) | 0 | = 0.0001 vs. controls<br>= 0.1843 vs. local BCNU<br>= 0.0168 vs. oral TMZ |
| 3.8% BCNU polymer + 50 mg/kg oral TMZ + XRT (n = 7) | 18 (18-26) | 0 | = 0.0001 vs. controls<br>= 0.05 vs. BCNU<br>= 0.0087 vs. oral TMZ<br>= 0.9639 vs. XRT |
| 3.8% BCNU polymer + 50% TMZ polymer (n = 7) | 18 (13-120) | 14.29 | = 0.001 vs. controls<br>= 0.1269 vs. local BCNU<br>= 0.0492 vs. oral TMZ<br>= 0.2124 vs. local TMZ |
| 3.8% BCNU polymer + 50% TMZ polymer + | 21 (14-25) | 0 | = 0.0004 vs. controls<br>= 0.0043 vs. local BCNU |

TABLE 3-continued

Treatment of the F98 experimental glioma model with locally delivered TMZ and BCNU and XRT

| Group | Median survival (days) | Long-term survivors (%) | P-values |
|---|---|---|---|
| XRT (n = 7) | | | = 0.0105 vs. local TMZ<br>= 0.0026 vs. oral TMZ<br>= 0.4116 vs. XRT |

Intracranial TMZ was administered at the maximal loading dose of the polymer (5 mg), and no signs of systemic toxicity or hematological dysfunction were observed, as compared with oral administration. Thus, local TMZ treatment increased intracranial TMZ concentrations in the tumor bed while minimizing systemic exposure to TMZ.

Clinically, both BCNU and TMZ have been shown to prolong the survival of patients with GBM. While each has a similar benefit alone, it was hypothesized that by combining these agents, there would be an additive benefit. To test this hypothesis, rats that were implanted with brain tumors were treated with TMZ, BCNU or a combination of both treatments. The results demonstrated that the concurrent local delivery of both BCNU and TMZ is superior to the use of either agent alone. No signs of systemic toxicity were observed. All patients with malignant gliomas are treated with some form of radiation therapy, making it crucial to determine the interaction of any chemotherapeutic strategies with XRT. The treatment groups received combinations including oral or local TMZ, local BCNU and XRT. The results confirmed the superiority of locally delivered TMZ polymers to orally administered TMZ (p=0.03) and the superiority of the combination of local BCNU and local TMZ compared to either treatment alone. These results were confirmed in both 9L experiments. The concomitant use of local BCNU, local TMZ and XRT proved better than all other treatment modalities with median survival not reached and 75% LTS. Although the superiority of the triple combination against the local administration of the two chemotherapeutic agents did not reach the level of statistical significance, it is possible that the small population studied did not give us enough data to demonstrate this. Several studies have supported a synergistic effect of BCNU and TMZ in the clinical treatment of gliomas: Menei et al., "Biodegradable carmustine-impregnated wafers (Gliadel®): the French experience". Presented at the 8th Congress of the European Association of Neurooncology, Barcellona, Spain, Sep. 12-14, 2008; McGirt et al., "Gliadel (BCNU) wafer plus concomitant temozolomide therapy after primary resection of glioblastoma multiforme". J Neurosurg (in press 2010); La Rocca et al. "A phase 2 study of multi-modal therapy with surgery, carmustine (BCNU) wafer, radiation therapy (RT), and temozolomide (TMZ) in patients (pts) with newly diagnosed supratentorial malignant glioma (MG)". Presented at the 8th Congress of the European Association of Neurooncology, Barcellona, Spain, Sep. 12-14, 2008; Gururangan "Phase I study of Gliadel wafers plus temozolomide in adults with recurrent supratentorial high-grade gliomas" Neuro Oncol 3:246-250, 2001; Pan et al. "A retrospective study of the safety of BCNU wafers with concurrent temozolomide and radiotherapy and adjuvant temozolomide for newly diagnosed glioblastoma patients" J Neurooncol 88:353-357, 2008.

There is evidence from pre-clinical trials in favor of a synergistic effect of BCNU and TMZ. See Plowman et al. Cancer Res 54:3793-3799, 1994; Lee et al. Br. J. Cancer 69:452-456, 1994. It has been hypothesized that this effect is probably mediated by the combined action of BCNU and TMZ that would maximize depletion of alkylguanine-DNA alkyltransferase (AGT), a DNA-repair protein found in the majority of human brain tumors (Wiestler et al. Carcinogenesis 5:121-124, 1984), and would eliminate the resistant tumor cells surrounding the resection cavity in the immediate postoperative period, during which early tumor repopulation can occur (Soffietti, et al. Anticancer Drugs 18:621-632, 2007). Hammond, et al. Clin Cancer Res 10:1645-1656, 2004, have shown a threefold decrease in AGT activity by the combination of BCNU and TMZ. This strategy takes advantage of the synergy between TMZ, BCNU and XRT, inhibiting sublethal damage induced by each modality alone (Soffietti, et al. 2007).

The results prove that in a rat glioma model local TMZ, local BCNU and XRT are better than the triple regimen containing oral TMZ, local BCNU and XRT (p=0.0033). The effectiveness of combined local administration is underlined even further when considering that this option provides 75% LTS and consequently does not reach median survival, whereas, the oral option resulted in a median survival of 62 days with 12.5% LTS.

In summary, the combination of intracranial TMZ polymer with intracranial BCNU polymer and radiation is safe and effective; the combination significantly prolongs survival compared to either treatment alone and to the currently clinical investigative treatment of oral TMZ, local BCNU and radiation in the 9L gliosarcoma model; the triple combination significantly prolongs survival compared to either treatment alone in the F98 glioma model.

Modifications and variations of the compositions and methods of use thereof will be apparent to those of skill in the art from the foregoing detailed description and are intended to fall within the scope of the appended claims. Cited references are specifically incorporated by reference herein.

We claim:

1. A composition for treating an individual with a solid tumor comprising a combination of carmustine and temozolomide
in a pharmaceutically acceptable polymeric carrier for sustained local administration of an effective amount of the carmustine and temozolomide to reduce tumor size or prolong survival of the individual with greater efficacy or reduced systemic side effects as compared to administration of either carmustine or temozolomide systemically.

2. The composition of claim 1 wherein the carrier is a polymeric wafer, disk, microparticle, or a microchip.

3. The composition of claim 1 wherein the carrier is a polymer comprising carmustine in a concentration range of 3.8-28% by weight.

4. The composition of claim 1 wherein the carrier is a polymer comprising temozolomide in a concentration range of 40-70% by weight.

5. The composition of claim 1 wherein the carrier is a polymer comprising 3.8% carmustine and 50% temozolomide.

6. A method of treating an individual with a tumor comprising administering the composition of claim 1.

7. The method of claim 6 wherein the individual has a brain tumor.

8. The method of claim 6 further comprising administering radiation to the individual.

* * * * *